United States Patent [19]

Kobayashi

[11] Patent Number: 5,446,115

[45] Date of Patent: Aug. 29, 1995

[54] SURFACE-TREATMENT COMPOSITION

[75] Inventor: Hideki Kobayashi, Chiba, Japan

[73] Assignee: Dow Corning Toray Silicon Co., LTD., Tokyo, Japan

[21] Appl. No.: 287,998

[22] Filed: Aug. 9, 1994

[30] Foreign Application Priority Data

Aug. 26, 1993 [JP] Japan .................. 5-234246

[51] Int. Cl.$^6$ .............................. C08G 77/08
[52] U.S. Cl. ........................ 528/18; 528/15; 528/17; 528/19; 528/31; 528/42; 428/446; 428/447
[58] Field of Search ............... 528/31, 42, 15, 17, 528/18, 19; 428/446, 447

[56] References Cited

U.S. PATENT DOCUMENTS

| | | | |
|---|---|---|---|
| 4,089,882 | 5/1978 | Takamizawa et al. | 260/448.2 |
| 4,968,828 | 11/1990 | Yamamoto | 556/448 |
| 5,099,053 | 3/1992 | Takaoka et al. | 556/448 |

FOREIGN PATENT DOCUMENTS

| | | |
|---|---|---|
| 753603 | 2/1967 | Canada . |
| 414186 | 2/1991 | European Pat. Off. . |
| 493747 | 7/1992 | European Pat. Off. . |
| 570943 | 11/1993 | European Pat. Off. . |
| 140388 | 3/1975 | Japan . |
| 140787 | 8/1982 | Japan . |
| 172245 | 11/1983 | Japan . |
| 255288 | 10/1988 | Japan . |
| 55781 | 2/1990 | Japan . |

Primary Examiner—Melvyn I. Marquis
Attorney, Agent, or Firm—Alexander Weitz

[57] ABSTRACT

A curable composition suitable for treating substrates in order to render them oil repellent, water repellent and stain resistant, said composition comprising:

(A) a fluorine-containing organosilicon compound having the general formula $$C_mF_{(2m+1)}-R^2-SiH_a R^1_{(3-a)}$$

wherein $R^1$ denotes a monovalent hydrocarbon group, excluding alkenyl groups, $R^2$ denotes a divalent organic group, a is 2 or 3, and m is an integer having a value of 4 to 12, or a partial hydrolysis and condensation product thereof, and (B) a catalytic quantity of a condensation-reaction catalyst.

16 Claims, No Drawings

SURFACE-TREATMENT COMPOSITION

FIELD OF THE INVENTION

The invention relates to a surface-treatment composition. More specifically, the invention relates to a surface-treatment composition that cures rapidly at the surface of a substrate to form thereon a film that exhibits an excellent water repellency, oil repellency, and stain resistance.

BACKGROUND OF THE INVENTION

It is already known that surface-treatment compositions based on fluorine-containing organosilicon compounds can impart water repellency, oil repellency, and stain resistance to the surfaces of substrates. As examples of such surface-treatment compositions, Japanese Patent Application Laid Open Number Sho 58-172245 teaches a surface-treatment composition that consists of perfluoroalkyl-containing silane (or its partial hydrolysis and condensation product) and a silane compound; Japanese Patent Application Laid Open Number Hei 2-55781 teaches a surface-treatment composition that consists of a fluorine-containing organosilicon compound (or its partial hydrolysis and condensation product) and an organoperoxide; and surface-treatment compositions composed of perfluoroalkyl-containing silanes are taught in Japanese Patent Application Laid Open Numbers Hei 2-138286, Hei 2-311485, and Hei 3-77892.

However, the surface-treatment composition taught in Japanese Patent Application Laid Open Number Sho 58-172245 has a poor curability at the surface of the substrate because it cures by the hydrolysis and condensation reactions of only Si-bonded alkoxy groups. Moreover, the film formed by this surface-treatment composition has a poor water repellency, oil repellency, and stain resistance. In the case of the surface-treatment composition taught in Japanese Patent Application Laid Open Number Hei 2-55781, the film formed on the surface of the substrate has a poor durability. Finally, the surface-treatment compositions taught in Japanese Patent Application Laid Open Numbers Hei 2-138286, Hei 2-311485, and Hei 3-77892 are limited in their range of application by their evolution of hydrogen halide by-product when the surface of the substrate is treated.

SUMMARY OF THE INVENTION

The present invention takes as its object the introduction of a surface-treatment composition that cures rapidly at the surface of a substrate to form thereon a film that exhibits an excellent water repellency, oil repellency, and stain resistance.

The invention relates to a surface-treatment composition comprising (A) a fluorine-containing organosilicon compound having the general formula $$C_mF_{(2m+1)}-R^2-SiH_a R^1_{(3-a)}$$

wherein $R^1$ denotes a monovalent hydrocarbon group, excluding alkenyl groups, $R^2$ denotes a divalent organic group, a is 2 or 3, and m is an integer having a value of 4 to 12, or the partial hydrolysis and condensation product thereof, and (B) a catalytic quantity of a condensation-reaction catalyst.

The surface-treatment composition in accordance with the present invention is explained in detail below.

The fluorine-containing organosilicon compound (A) is the basic active ingredient in the present composition, and it has the general formula $$C_mF_{(2m+1)}-R^2-SiH_a R^1_{(3-a)}$$

wherein $R^1$ denotes a monovalent hydrocarbon group, excluding alkenyl groups. $R^1$ is specifically exemplified by alkyl groups such as methyl, ethyl, propyl, butyl, and pentyl; aryl groups such as phenyl, tolyl, and xylyl; and aralkyl groups such as benzyl, and phenethyl. Methyl and phenyl are preferred for $R^1$. $R^2$ in the preceding formula denotes a divalent organic group. $R^2$ is specifically exemplified by alkylene groups such as ethylene, methylmethylene, propylene, and butylene; alkyleneoxyalkylene groups such as methyleneoxyethylene, methyleneoxypropylene, and ethleneoxypropylene; arylenealkylene groups such as phenyleneethylene, phenylenepropylene, and phenylenebutylene; and aryleneoxyalkylene groups such as phenyleneoxyethylene, and phenyleneoxypropylene. Ethylene and propylene are preferred for $R^2$.

The subscript a in the preceding formula has a value of 2 or 3. When a has a value of 2, component (A) is a fluorinated organic group-containing dihydrogensilane. When a has a value of 3, component (A) takes the form of a fluorinated organic group-containing trihydrogensilane. The subscript m in the preceding formula is an integer with a value of 4 to 12, and values of 4, 6, 8, and 12 are preferred. The fluorine-containing organosilicon compounds in which m is less than 4 have a surface tension, chemical resistance, water repellency, and oil repellency inferior to that of the fluorine-containing organosilicon compounds encompassed by component (A). On the other hand, the fluorine-containing organosilicon compounds in which m exceeds 12 are very difficult to handle and have limited applications.

No specific restrictions apply to the structural configuration of the perfluoroalkyl group $C_mF_{(2m+1)}$- in the fluorine-containing organic group of component (A), and this group may be, for example, straight chain, branched, or a partially branched straight chain. The straight chain configuration is preferred.

The fluorine-containing organosilicon compounds comprising component (A) are specifically exemplified by fluorine-containing organosilicon compounds with the following structures.

$C_4F_9C_2H_4SiH_3$
$C_6F_{13}C_3H_6SiH_3$
$C_8F_{17}C_2H_4SiH_3$
$C_4F_9C_2H_4Si(CH_3)H_2$
$C_6F_{13}C_2H_4Si(CH_3)H_2$
$C_8F_{17}C_2H_4Si(CH_3)H_2$
$C_4F_9CH_2OC_2H_4SiH_3$
$C_6F_{13}CH_2OC_3H_6SiH_3$
$C_8F_{17}C_2H_4OC_2H_4SiH_3$
$C_4F_9CH_2)C_2H_4Si(CH_3)H_2$
$C_6F_{13}CH_2OC_2H_4Si(CH_3)H_2$
$C_8F_{17}CH_2OC_2H_4Si(CH_3)H_2$

The state of component (A) is not specifically restricted, and component (A) is, for example, a liquid or wax at room temperature. Component (A) can be easily handled, but at the same time it is characterized by a very high reactivity due to the presence of 2 or more silicon-bonded hydrogen atoms in each molecule. Given this high reactivity, to the extent that the object of the invention is not impaired, a component (A) may be used whose silicon-bonded hydrogens have in part already undergone hydrolysis and condensation reactions.

The method for synthesizing component (A) is not specifically restricted. In one example of the synthesis of component (A), a platinum-catalyzed addition reaction is first run between an organosilicon compound such as trichlorosilane, tribromosilane, methyldichlorosilane, ethyldichlorosilane, propyldichlorosilane, phenyldichlorosilane, methyldibromosilane, ethyldibromosilane, propyldibromosilane, and phenyldibromosilane, and a fluorinated organic compound such as

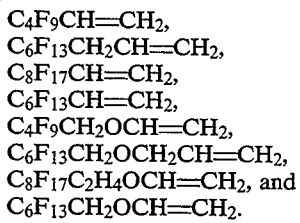

$C_4F_9CH=CH_2$,
$C_6F_{13}CH_2CH=CH_2$,
$C_8F_{17}CH=CH_2$,
$C_6F_{13}CH=CH_2$,
$C_4F_9CH_2OCH=CH_2$,
$C_6F_{13}CH_2OCH_2CH=CH_2$,
$C_8F_{17}C_2H_4OCH=CH_2$, and
$C_6F_{13}CH_2OCH=CH_2$.

Suitable catalysts for this addition reaction are chloroplatinic acid, alcohol solutions of chloroplatinic acid, platinum-olefin complexes, platinum-alkenylsiloxane complexes, and so forth. Component (A) is then obtained by reducing the addition-reaction product with a reducing agent such as lithium aluminum hydride, sodium aluminum hydride, lithium hydride, $Al(BH_4)_3$, sodium dihydrobis(methoxyethoxy) aluminate, or the like. Further details of the preparation of Component (A) may be found in U.S. patent application Ser. No. 08/213,396, filed on Mar. 14, 1994, Pat. No. 5,374,760, and hereby incorporated by reference.

The condensation-reaction catalyst (B) is a catalyst that accelerates the cure of the subject composition, and it also functions to increase the adherence of the film to the surface of the substrate. Any compound ordinarily known as a condensation-reaction catalyst can be used as component (B). Component (B) is specifically exemplified by tetraalkyl titanates such as tetra-n-butyl titanate; complexes of dialkyl titanates; organosiloxy titanates; the tin salts of carboxylic acids such as dibutyltin acetate, dibutyltin laurate, dibutyltin dioctoate, stannous octoate, stannous naphthenate, stannous oleate, stannous isobutyrate, stannous linoleate, stannous stearate, stannous benzoate, stannous naphthoate, stannous laurate, stannous othymate, stannous beta-benzoylpropionate, stannous crotonate, stannous tropate, stannous p-bromobenzoate, stannous palmitoleate, stannous cinnamate, and stannous phenylacetate; and by the iron salts, manganese salts, and cobalt salts of the preceding carboxylic acids.

Component (B) is added to the invention composition in a catalytic quantity. While its quantity of addition is not otherwise specifically restricted, it is preferably added at a level of 0.01 to 20 weight parts per 100 weight parts component (A). The addition of less than about 0.01 weight parts component (B) per 100 weight parts component (A) results in a gradual decline in the curability of the composition. At the other extreme, the addition of more than about 20 weight parts component (B) per 100 weight parts component (A) causes a gradual decline in the film strength.

The invention composition itself is prepared by mixing components (A) and (B) to homogeneity. In addition, the invention composition can be formulated as an organic solvent solution or water-based emulsion for the purpose of its actual application. Organic solvents that can be added on an optional basis in order to prepare the organic solvent solution of the invention composition are nonexhaustively exemplified by ether solvents such as dimethyl ether, diethyl ether, and tetrahydrofuran; ketone solvents such as methyl ethyl ketone, and methyl isobutyl ketone; aliphatic hydrocarbon solvents such as hexane, and heptane; and aromatic hydrocarbon solvents such as toluene, and xylene. In order to use the invention composition formulated as the water-based emulsion, water and a surfactant can be added.

No particular restrictions apply to the substrates to which the invention composition can be applied. The composition of the invention can be applied, for example, to inorganic powders such as silica micropowder, titanium oxide powder, aluminum oxide powder, iron oxide powder, zinc oxide powder, calcium carbonate powder, zirconium carbonate powder, and zinc carbonate powder; the powders of organic resins such as polyester powders, polycarbonate powders, polystyrene powders, acrylic powders, methacrylic powders, nylon powders, fluororesin powders, and silicone powders; glass plate, for example, of soda glass, heat-reflecting glass, automotive glass, glass for marine and aeronautical applications, and so forth; metal sheet, for example, of copper, iron, stainless steel, aluminum, zinc, and so forth; paper such as high-grade paper, ordinary Japanese straw writing paper, and so forth; synthetic plastic films of, for example, polyester, polycarbonate, polystyrene, acrylic resin, and so forth; and to fabrics and textiles, ceramics, plastics, papers, natural fibers, and synthetic fibers.

No specific restrictions apply with regard to the technique for treating the substrate surface with the invention composition. For example, the composition can be applied by immersion, spray application, or brush application. A water-repellent, oil-repellent, and stain-resistant film can be formed on the substrate surface by first uniformly applying the composition on the surface of the substrate, then eliminating any organic solvent or water at room temperature or by heating, and thereafter curing the composition itself at room temperature or by heating. While no specific restrictions apply to the conditions for forming the film on the substrate surface, heating for 20 seconds to 3 hours at temperatures of 50° C. to 150° C. is preferred.

Films prepared as described above have a low surface tension and an excellent water repellency, oil repellency, and resistance to staining. The treatment of natural or synthetic fiber with the invention composition characteristically yields a long-lasting water repellency, oil repellency, and stain resistance while at the same time giving a treated fabric that is soft and flexible.

EXAMPLES

The surface-treatment composition in accordance with the present invention will be explained in greater detail with reference to working examples. The contact angle was measured at room temperature (22° C.) by the droplet method using a contact angle meter from Kyowa Kaimen Kagaku Kabushiki Kaisha. The average of the contact angles measured at five locations on the film is reported as the contact angle of the film.

Example 1

Ten grams of 2-(perfluorooctyl)ethylsilane ($C_8F_{17}C_2H_4SiH_3$) 0.02 g of dibutyltin diacetate, and 100 g of toluene were mixed to homogeneity to yield a surface-treatment composition in accordance with the present invention. This composition was uniformly applied to a smooth, flat glass plate, air-dried at room temperature for 1 hour, and finally heated at 150° C. for 1 hour to yield a film on the glass plate. The contact angles for this film were measured with the following results: the water contact angle was 120° and the hexadecane contact angle was 70°.

A fabric of 100% processed polyester yarn was immersed in the above composition for 10 seconds and then wrung out to give a silicon add-on level of 0.4% (weight). The fabric was subsequently air-dried at room temperature and thereafter heated for 3 minutes at 150° C. to yield a film on the surface of the fabric. Water and salad oil were dripped onto the treated fabric, and the repellency was extremely good in both cases. The treated fabric was also very soft and flexible.

Example 2

Ten grams of 2-(perfluorobutyl)ethylsilane $C_4F_9C_2H_4SiH_3$, 0.02 of g dibutyltin diacetate, and 100 g of hexane were mixed to homogeneity to yield a surface-treatment composition in accordance with the present invention. This composition was uniformly applied to a smooth, flat glass plate, air-dried at room temperature for 1 hour, and finally heated at 150° C. for 1 hour to yield a film on the glass plate. The contact angles for this film were measured as in Example 1 with the following results: the water contact angle was 118° and the hexadecane contact angle was 69°.

A fabric of 100% processed polyester yarn was immersed in the composition for 10 seconds and then wrung out to give a silicon add-on of 0.4% (weight). The fabric was subsequently air-dried at room temperature and thereafter heated for 3 minutes at 150° C. to yield a film on the surface of the fabric. Water and salad oil were dripped onto the treated fabric, and the repellency was extremely good in both cases. The treated fabric was also very soft and flexible.

I claim:

1. A composition comprising:
   (A) a component selected from the group consisting of a fluorine-containing organosilicon compound having the general formula $$C_mF_{(2m+1)}-R^2-SiH_a R^1_{(3-a)}$$

wherein $R^1$ denotes a monovalent hydrocarbon group, excluding alkenyl groups, $R^2$ denotes a divalent organic group, a is 2 or 3, and m is an integer having a value of 4 to 12, and a partial hydrolysis and condensation product of said fluorine-containing organosilicon compound; and
   (B) a catalytic quantity of a condensation-reaction catalyst.

2. The composition according to claim 1, wherein m is 4, 6, 8 or 12.

3. The composition according to claim 2, wherein said fluorine-containing organosilicon compound (A) is represented by a formula selected from the group consisting of
$C_4F_9C_2H_4SiH_3$,
$C_6F_{13}C_3H_6SiH_3$,
$C_8F_{17}C_2H_4SiH_3$,
$C_4F_9C_2H_4Si(CH_3)H_2$,
$C_6F_{13}C_2H_4Si(CH_3)H_2$,
$C_8F_{17}C_2H_4Si(CH_3)H_2$,
$C_4F_9CH_2OC_2H_4SiH_3$,
$C_6F_{13}CH_2OC_3H_6SiH_3$,
$C_8F_{17}C_2H_4OC_2H_4SiH_3$,
$C_4F_9CH_2OC_2H_4Si(CH_3)H_2$,
$C_6F_{13}CH_2OC_2H_4Si(CH_3)H_2$, and
$C_8F_{17}CH_2OC_2H_4Si(CH_3)H_2$.

4. The composition according to claim 3, wherein said catalyst (B) is selected from the group consisting of tetraalkyl titanates, complexes of dialkyl titanates; organosiloxy titanates, tin salts of carboxylic acids, iron salts of carboxylic acids, manganese salts of carboxylic acids, and cobalt salts of carboxylic acids.

5. The composition according to claim 1, wherein said catalyst (B) is selected from the group consisting of tetraalkyl titanates, complexes of dialkyl titanates; organosiloxy titanates, tin salts of carboxylic acids, iron salts of carboxylic acids, manganese salts of carboxylic acids, and cobalt salts of carboxylic acids.

6. The composition according to claim 1, wherein said catalyst (B) is selected from the group consisting of tetra-n-butyl titanate, dibutyltin acetate, dibutyltin laurate, dibutyltin dioctoate, stannous octoate, stannous naphthenate, stannous oleate, stannous isobutyrate, stannous linoleate, stannous stearate, stannous benzoate, stannous naphthoate, stannous laurate, stannous o-thymate, stannous beta-benzoylpropionate, stannous crotonate, stannous tropate, stannous p-bromobenzoate, stannous palmitoleate, stannous cinnamate and stannous phenylacetate.

7. The composition according to claim 1, wherein $R^1$ is a methyl radical.

8. The composition according to claim 3, wherein said catalyst (B) is selected from the group consisting of tetra-n-butyl titanate, dibutyltin acetate, dibutyltin laurate, dibutyltin dioctoate, stannous octoate, stannous naphthenate, stannous oleate, stannous isobutyrate, stannous linoleate, stannous stearate, stannous benzoate, stannous naphthoate, stannous laurate, stannous o-thymate, stannous beta-benzoylpropionate, stannous crotonate, stannous tropate, stannous p-bromobenzoate, stannous palmitoleate, stannous cinnamate and stannous phenylacetate.

9. A substrate having thereon a film of the composition of claim 1.

10. A substrate having thereon a film of the composition of claim 2.

11. A substrate having thereon a film of the composition of claim 3.

12. A substrate having thereon a film of the composition of claim 4.

13. A substrate having thereon a film of the composition of claim 5.

14. A substrate having thereon a film of the composition of claim 6.

15. A substrate having thereon a film of the composition of claim 7.

16. A substrate having thereon a film of the composition of claim 8.

* * * * *